United States Patent
Scheffold et al.

(10) Patent No.: US 8,709,710 B2
(45) Date of Patent: Apr. 29, 2014

(54) METHODS OF MODULATING INTERLEUKIN-22 AND IMMUNE RESPONSE BY NOTCH REGULATORS

(75) Inventors: Alexander Scheffold, Cologne (DE); Sascha Rutz, Berlin (DE); Frederick Heinrich, Berlin (DE)

(73) Assignee: Deutsches Rheuma-Forschungszentrum Berlin, Berlin (DE)

( * ) Notice: Subject to any disclaimer, the term of this patent is extended or adjusted under 35 U.S.C. 154(b) by 90 days.

(21) Appl. No.: 13/201,638

(22) PCT Filed: Feb. 16, 2010

(86) PCT No.: PCT/DE2010/000212
§ 371 (c)(1),
(2), (4) Date: Oct. 26, 2011

(87) PCT Pub. No.: WO2010/091679
PCT Pub. Date: Aug. 19, 2010

(65) Prior Publication Data
US 2012/0045458 A1    Feb. 23, 2012

(30) Foreign Application Priority Data
Feb. 16, 2009 (DE) .................. 10 2009 009 603

(51) Int. Cl.
| | | |
|---|---|---|
| *G01N 33/53* | (2006.01) | |
| *G01N 33/68* | (2006.01) | |
| *C12P 21/02* | (2006.01) | |
| *C12N 5/07* | (2010.01) | |
| *A61K 38/16* | (2006.01) | |
| *C07K 14/54* | (2006.01) | |
| *C07K 14/475* | (2006.01) | |
| *C07K 14/705* | (2006.01) | |

(52) U.S. Cl.
USPC ............ 435/4; 435/7.1; 435/70.1; 435/372.3; 530/350; 530/351; 424/184.1

(58) Field of Classification Search
None
See application file for complete search history.

(56) References Cited

U.S. PATENT DOCUMENTS

| | | | | |
|---|---|---|---|---|
| 6,887,475 | B1* | 5/2005 | Lamb et al. | ............... 424/184.1 |
| 2003/0194804 | A1* | 10/2003 | Lamb et al. | ................... 435/372 |
| 2010/0136022 | A1 | 6/2010 | Scheffold | |

FOREIGN PATENT DOCUMENTS

| | | |
|---|---|---|
| WO | 98/20142 A1 | 5/1998 |
| WO | 02/096952 A2 | 12/2002 |
| WO | 03/011317 A1 | 2/2003 |
| WO | 2008/092445 A2 | 8/2008 |

OTHER PUBLICATIONS

Alam et al. Notch signaling drives IL-22 secretion in CD4+ T cells by stimulating the aryl hydrocarbon receptor. Proc Natl Acad Sci USA 107(13): 5943-5948, Mar. 20, 2010.*
Kassner et al. Cutting edge: plasmacytoid dendritic cells induce IL-10 production in T cells via the delta-like-4/Notch axis. J Immunol 184: 550-554, 2010.*
Neumann et al. Self-control of pathogenic T helper cells can be activated via the notch signalling pathway. Zeitschrift fur Rheumatologie 71(Suppl 2): 40, 2012.*
Rutz et al. Notch regulates IL-10 production by T helper 1 cells. Proc Natl Acad Sci 105(9): 3497-3502, 2008.*
Rutz et al. Regulation of interleukin-10 and interleukin-22 expression in T helper cells. Curr Opin Immunol 23: 605-612, 2011.*
Wilson et al. Epigenetic control of T-helper-cell differentiation. Nature Rev 9(2): 91-105, Feb. 2009.*
Mukherjee et al. Regulation of T cell activation by notch ligand, DLL4, promotes IL-17 production and Rorc activation. J Immunol 182: 7381-7388, Jun. 2009.*
Anastasi Emanuela et al: "Expression of activated Notch3 in transgenic mice enhances generation of T regulatory cells and protects against experimental autoimmune diabetes" in: Journal of Immunology, American Association of Immunologists, US, vol. 171, No. 9, Nov. 1, 2003, pp. 4504-4511.

* cited by examiner

*Primary Examiner* — Bridget E Bunner
(74) *Attorney, Agent, or Firm* — Joyce von Natzmer; Agris & von Natzmer LLP

(57) ABSTRACT

The invention relates to the use of notch regulators for modulating IL-22 production in T-cells, by influencing the activity or activation of the notch signal path. The invention further relates to the use of modulating the immune response, primarily in case of infection reactions. The invention in particular relates to the use for treating illnesses associated with infections. The invention further relates to the use for reducing IL-22 production in T-cells.

19 Claims, 6 Drawing Sheets

METHODS OF MODULATING INTERLEUKIN-22 AND IMMUNE RESPONSE BY NOTCH REGULATORS

CROSS-REFERENCE TO RELATED APPLICATIONS

This is the U.S. national stage of International application PCT/DE2010/000212, filed Feb. 16, 2010 designating the United States and claims priority to German patent application DE 10 2009 009 603.5, filed Feb. 16, 2009.

DESCRIPTION

The invention relates to a method for the specific modulation of interleukin-22 expression of T-cells by influencing the Notch signaling pathway. The invention comprises:

1. a means of generating interleukin (IL)-22-producing T cells by activating the Notch signaling pathway;
2. a means of inhibiting the IL-22 expression of T-cells by inhibiting the Notch signaling pathway.

The invention also relates to the use of Notch regulators for modulating inflammatory reactions. More specifically, the invention relates to the aforesaid use for the treatment of diseases associated with inflammation.

In accordance with the diverse functions of T helper cells, there are different subpopulations of these cells. They are remarkable for their differential expression of soluble messenger molecules, i.e. the cytokines.

One subpopulation of T helper cells, the so-called Th1 cells, express cytokines which are able to direct the cellular immune response, including interferon (IFN)-γ and tumor necrosis factors (TNF)-α and β. Th2 cells are required for humoral immune responses. The Th2 cytokines include IL-4, IL-5, IL-10 and IL-13. Another subpopulation of T helper cells, the so-called Th17 cells, are characterized by the production of the IL-17 cytokine and likewise have a pro-inflammatory effect.

IL-22 has no effect on leukocytes, but rather on hepatocytes, keratinocytes or intestinal epithelial cells. IL-22 is involved in inflammatory processes, but also in tissue repair and wound healing.

IL-22 induces pro-inflammatory responses by inducing cytokines, chemokines and acute-phase proteins in many cell types. In addition, IL-22 induces the production of antimicrobial peptides such as β-defensins and S100 proteins. It can induce strong antimicrobial response in vitro and is associated with various viral and bacterial infections.

The function of IL-22 in inflammatory processes depends crucially on the target tissue. Although there are some reports of a pro-inflammatory pathogenic function of IL-22 primarily in inflammatory reactions of the skin (IL-22 is overexpressed in psoriatic lesions), a protective effect has been found in other systems. IL-22 has a protective effect in hepatitis or ulcerative colitis.

Up to now, IL-22 has been described primarily as a Th17 cytokine. On the other hand, IL-22 is also expressed by NK cells and dendritic cells.

IL-22 can be induced by IL-23 and IL-6 in Th cells in vitro, while TGF-β has an inhibiting effect. It is primarily IL-23 that is required for IL-22 expression in vivo. The molecular mechanisms are unknown as yet.

BRIEF DESCRIPTION OF THE FIGURES

FIG. 2B: Th17 cells).

FIG. 5 shows in FIG. 5A specific inhibition of the Notch signaling pathway by a specific inhibitor (γ-secretase inhibitor), while FIG. 5B shows selective inhibition of the interaction of Notch with Jagged or with Dll-1 and Dll-4 by blocking antibodies.

DESCRIPTION OF VARIOUS AND PREFERRED EMBODIMENTS

Figure 1:
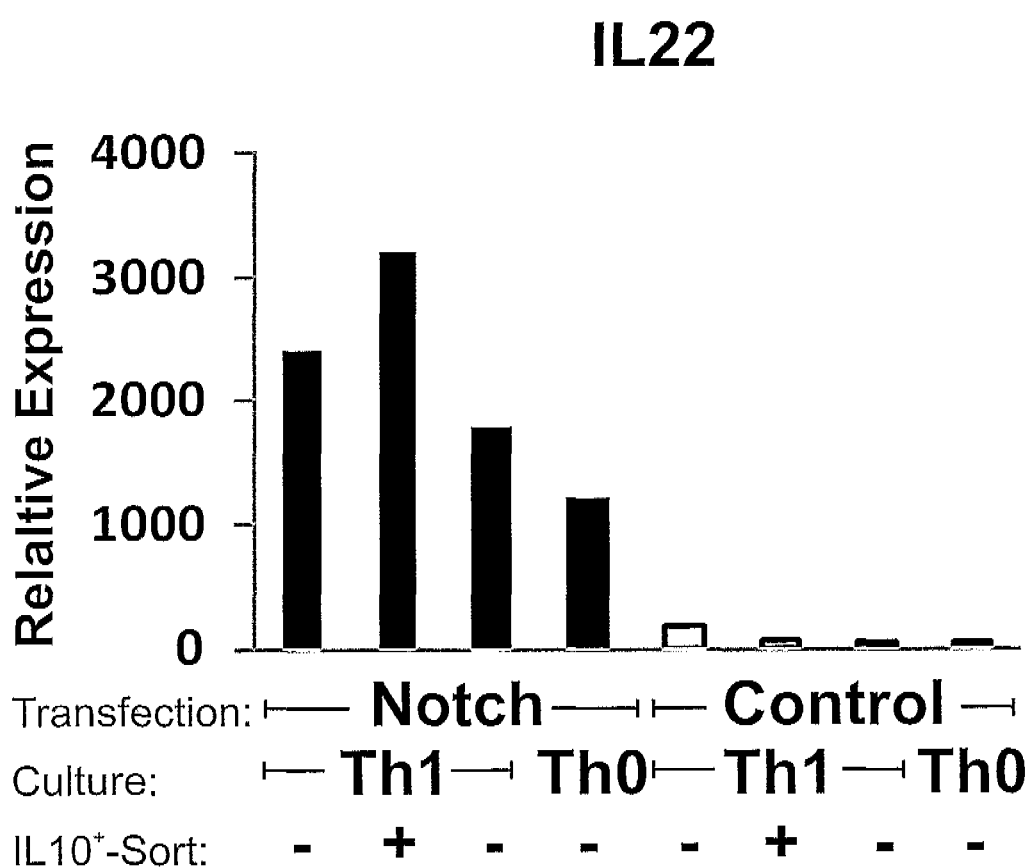
FIG. 1 shows IL-22 production by both IL-10-positive and IL-10-negative Th cells.

As IL-22 plays a role in many processes, including, inter alia, the course of various diseases, the object of the invention was to regulate, in particular enhance or switch off, the production of IL-22 in T cells.

Said object was accomplished by means of the embodiments of the claims.

In a first embodiment the invention relates to the use of Notch regulators selected from the group comprising inducers of signal-active Notch molecules and/or Notch inhibitors for modifying the interleukin-22 production in T cells.

It was quite surprising that regulation of the Notch signaling pathway can be used to modulate the production of IL-22 in T cells. Advantageously, Notch regulators in the meaning of the invention do not trigger any side effects and can therefore be used very safely for regulating the IL-22 production.

Also preferred is a use which is characterized in that the T cells are selected from the group comprising naive T cells, memory T cells, pro-inflammatory Th1 cells, pro-inflammatory Th2 cells and pro-inflammatory Th17 cells. It was quite surprising to find that regulation of the Notch signaling pathway in these cells results in modulation of the IL-22 production.

Notch is always present in a cell in latent form. This latent form is converted into an (signal) active (signal-active=active) form by activators. In the event of a Notch receptor this proceeds by proteolytic cleavage. This also implies that the active form is different in structure/nature from the latent form.

Thus, a signal-active form can be conveyed into a cell on two routes:

a) By physiological activation of receptors: activators of Notch according to this definition are Notch ligands, Notch ligand proteins, Notch ligand fusion proteins, Notch ligand fragments, Notch ligand-expressing cells and/or stimulatory anti-Notch antibodies.

b) By direct transfection of cells with the constitutively active form of Notch (Notch intracellular domain (NICD)), preferably Notch receptors 1, 2, 3 or 4.

The inducers of signal-active Notch molecules are preferably selected from the group comprising activators for Notch, preferably Notch ligands, Notch ligand proteins, Notch ligand fusion proteins, Notch ligand fragments, Notch ligand-expressing cells and/or stimulatory anti-Notch antibodies and/or Notch receptors, preferably Notch receptors 1, 2, 3 or 4.

In addition, the use of endogenous Notch molecules is advantageous. Endogenous Notch molecules have the advantage of acting specifically on a single cell, thereby allowing precise regulation.

The Notch receptors are preferably selected from the group comprising Notch 1, 2, 3 and/or 4.

The Notch ligands are preferably selected from the group comprising the Jagged family, in particular Jagged 1 and/or 2, and/or the Delta-like family, especially Delta-like 1, 2 and/or 4.

It was surprising that Notch ligands of the Delta-like family, especially Delta-like 4, bring about IL-22 induction.

It was also surprising that pDC, in particular following stimulation with ligands of Toll-like receptors, preferably TLR 1-13 and in particular TLR 9, express particularly large quantities of Delta-like 4 and under these conditions give particularly efficient induction of IL-22 in T cells.

Notch ligand fragments and protein fragments are those as disclosed in WO 2004/024764 A1. The Notch ligand constructs and fragments disclosed therein can be used for either activation or inhibition of the Notch signaling pathway. In a preferred fashion the fragments have essentially the same activity as the molecules from which they have been obtained.

The inhibitors of Notch activation are preferably selected from the group comprising recombinant proteins, protein fragments and/or peptides of Notch or Notch ligands, pharmacological inhibitors, preferably γ-secretase inhibitors, antibodies against Notch molecules for inhibiting induction and/or expression of interleukin-22.

In a preferred embodiment the invention relates to the use of signal-active Notch molecule inducers and/or signal-active Notch molecules for generating interleukin-22-producing T cells.

It was surprising that T cells express IL-22 when contacted with signal-active Notch.

Also preferred is the use of signal-active Notch molecule inducers and/or signal-active Notch molecules for inducing and/or expressing interleukin-22.

In a particularly preferred fashion the T cells are contacted with signal-active Notch molecules. Activation of Notch induces IL-22 production of T cells.

Also preferred is a use wherein signal-active Notch 1, 2, 3 and/or 4 are overexpressed. Said use results in a particularly rapid increase in IL-22 production. A person skilled in the art will be familiar with methods to induce overexpression of particular proteins and produce signal-active variants of proteins.

Contacting endogenous Notch molecules with Notch ligands is also advantageous. A person skilled in the art will be familiar with methods of contacting endogenous Notch molecules with Notch ligands in such a way that the Notch signaling pathway is activated.

Also preferred is a use wherein Notch ligands are contacted with T cells, said contacting being enhanced and/or induced by stimulation with cells, which cells are selected from the group comprising antigen-presenting cells, in particular by stimulation of antigen-presenting cells with Toll-like receptors or CD40 and/or plasmacytoid dendritic cells, in particular by stimulating plasmacytoid dendritic cells via Toll-like receptors or CD40.

A person skilled in the art will be familiar with methods to activate TLR. In a preferred fashion the ligands are molecules of the Delta-like family, especially Delta-like 4 and/or Delta-like 1. In particular, the TLRs are molecules selected from the group comprising TLR 1, 2, 3, 4, 5, 6, 7, 8, 9, 10, 11, 12 and/or 13.

In a particularly preferred embodiment of the invention, contacting with Notch ligands is effected by stimulation with plasmacytoid dendritic cells, said contacting being enhanced and/or induced particularly via TLR. Plasmacytoid dendritic cells give particularly high levels of Delta-like 1 and 4 Notch ligand expression.

In another preferred embodiment the invention relates to the use of signal-active Notch molecule inducers and/or signal-active Notch molecules, wherein interleukin-22-producing T cells are generated by in vitro stimulation with Notch ligand proteins, Notch ligand fusion proteins, signal-active Notch ligand fragments, Notch ligand-expressing cells and/or by introducing signal-active Notch using viral and/or non-viral transduction methods. The uses according to the invention result in greatly increased IL-22 expression rates.

It is envisaged in another preferred embodiment of the invention that generating the IL-22-producing T cells is effected in vivo by using recombinant Notch ligands and/or Notch ligand fusion proteins and/or signal-active Notch ligand fragments and/or by using Notch ligand-expressing cells. Among Notch ligand-expressing cells, plasmacytoid dendritic cells are particularly suitable to this end. This embodiment of the invention is particularly advantageous because it implies safe and effective use and achieves this particularly high expression rate.

In another preferred embodiment the invention relates to the use of signal-active Notch molecule inducers and/or signal-active Notch molecules in the production of a medicament for the induction and/or expression of interleukin-22, preferably for the modulation of inflammatory reactions.

Particularly good results were achieved with the use of signal-active Notch molecule inducers and/or signal-active Notch molecules in the production of a pharmaceutical agent for the treatment of inflammatory diseases, hepatitis, colitis, inflammation of the gastrointestinal tract and/or autoimmune diseases. The production of IL-22 resulted in significantly improved overall conditions of patients.

Being particularly well tolerable and free of side effects, signal-active Notch molecules are particularly well suited for the production of a pharmaceutical agent.

In another preferred embodiment the invention relates to a method of generating interleukin-22-producing T cells. In the method according to the invention, T cells are contacted with signal-active Notch molecules to thereby activate the Notch signaling pathway. The method is advantageous because it can be used particularly easily and efficiently. The easy implementation saves cost, time and processing steps.

In another preferred embodiment the invention relates to the use of inhibitors of Notch activation selected from the group comprising recombinant proteins, protein fragments and/or peptides of Notch or Notch ligands, pharmacological inhibitors, preferably γ-secretase inhibitors, antibodies against Notch molecules for inhibiting induction and/or expression of interleukin-22.

In particular, pharmacological inhibitors of the Notch signaling pathway comprise substances of the class of γ-secretase inhibitors.

In addition, other inhibitors of the Notch signaling pathway should be included, such as soluble Notch ligands, their fragments, fusion proteins, or single peptides such as disclosed in WO 2004/024764. More specifically, naturally blocking antibodies against Notch receptors are claimed as well. Inhibition of Notch activation is also possible by transfection of cells with negative regulators of the Notch signaling pathway. In this context, Deltex, MINT, NRARP or dominant-negative forms of Mastermind are preferred agents well-known to those skilled in the art.

It was quite surprising that blocking the Notch signaling pathway reduces or switches off the production of IL-22 by T cells, preferably pro-inflammatory T cells.

The use is preferably characterized in that expression of Notch ligands of the Delta-like family, especially of the Delta-like 1 and Delta-like 4 ligands, is inhibited in antigen-presenting cells and/or dendritic cells.

Also preferred is the use of Notch regulators in the production of a pharmaceutical agent for the modulation of IL-22 production in T cells.

As IL-22 plays a role in quite a number of diseases, a medicament that regulates the production of IL-22 can be used in the treatment, diagnosis or prophylaxis of a wide variety of diseases such as AIDS, acne, albuminuria (proteinuria), alcohol withdrawal syndrome, allergies, alopecia (loss of hair), ALS (amyotrophic lateral sclerosis), Alzheimer's disease, ALS (senile macular retinal degeneration), anemia, particularly pernicious anemia, anxiety syndrome, anthrax (milzbrand), aortic sclerosis, occlusive arterial disease, arteriosclerosis, arterial occlusion, arteriitis temporalis, arteriovenous fistula, arthritis, arthrosis, asthma, respiratory insufficiency, autoimmune disease, atrioventricular block, acidosis, prolapsed intervertebral disc, inflammation of the peritoneum, pancreatic cancer, Becker muscular dystrophy, benign prostate hyperplasia (BPH), bladder carcinoma, hemophilia, bronchial carcinoma, breast cancer, BSE, Budd-Chiari syndrome, bulimia nervosa, bursitis, Byler syndrome, bypass, chlamydia infection, chronic pain, cirrhosis, commotio cerebri (brain concussion), Creutzfeld-Jacob disease, intestinal carcinoma, intestinal tuberculosis, depression, diabetes insipidus, diabetes mellitus, diabetes mellitus juvenilis, diabetic retinopathy, Duchenne muscular dystrophia, duodenal carcinoma, dystrophia musculorum progressiva, dystrophia, ebola, eczema, erectile dysfunction, obesity, fibrosis, cervix cancer, uterine cancer, cerebral hemorrhage, encephalitis, loss of hair, hemiplegia, hemolytic anemia, hemophilia, pet allergy (animal hair allergy), skin cancer, herpes zoster, cardiac infarction, cardiac insufficiency, cardiovalvulitis, cerebral metastases, cerebral stroke, cerebral tumor, testicle cancer, ischemia, Kahler's disease (plasmocytoma), polio (poliomyelitis), rarefaction of bone, contact eczema, palsy, liver cirrhosis, leukemia, pulmonary fibrosis, lung cancer, pulmonary edema, lymph node cancer, (Hodgkin's disease), lymphogranulomatosis, lymphoma, lyssa, gastric carcinoma, mammary carcinoma, meningitis, milzbrand, mucoviscidosis (cystic fibrosis), multiple sclerosis (MS), myocardial infarction, neurodermitis, neurofibromatosis, neuronal tumors, kidney cancer (kidney cell carcinoma), osteoporosis, pancreas carcinoma, pneumonia, polyneuropathies, potency disorders, progressive systemic sclerosis (PSS), prostate cancer, urticaria, traumatic paraplegic syndrome, rectum carcinoma, pleurisy, craniocerebral trauma, vaginal carcinoma, sinusitis, esophageal cancer, tremor, tuberculosis, tumor pain, vaginal carcinoma, burns/scalds, intoxications, viral meningitis, menopause, soft-tissue sarcoma, soft-tissue tumor, cerebral blood circulation disorders and/or CNS tumors, Hashimoto's thyroiditis, primary myxedema, thyrotoxicosis (Basedow's disease), Addison's disease, myasthenia gravis, Goodpasture's syndrome, autoimmune hemolytic anemia, autoimmune leukopenia, pemphigus vulgaris, sympathetic ophthalmia, primary biliary cirrhosis, in particular primary biliary liver cirrhosis, autoimmune hepatitis, especially chronic aggressive autoimmune hepatitis, Sjogren's syndrome, rheumatoid arthritis, rheumatic fever, systemic lupus erythematosus, dermatomyositis/polymyositis, progressive systemic sclerosis, Wegener's granulomatosis, polyarteritis nodosa, hypersensitivity angiitis, thyrotoxicosis, thyroid-caused myxedema, generalized endocrinopathy, chronic gastritis type A, autoimmune diseases of single or all corpuscular elements of the blood, particularly idiopathic thrombocytopenia or thrombocytopathy, idiopathic leukopenia, agranulocytosis, pemphigoid, uveitis, diabetes mellitus type I, Crohn's disease, ulcerative colitis, Addison's disease, lupus erythematosus disseminatus and discoid form of said disease, as dermatomyositis and scleroderma, rheumatoid arthritis (=primary chronic polyarthritis), antiglomerular basement membrane nephritis, an aggressive immune reaction due to breakdown of the immune tolerance to self-determinants and reduction of the activity of T suppressor cells, preferably with lymphocyte marker T8 or excess of T helper cells, preferably with lymphocyte marker T4 via suppressor cells; formation of autoantigens, particularly by coupling of host proteins to haptens, preferably drugs, immune reactions caused by ontogenetic tissue not developing until self-tolerance has developed, by protein components demasked as a result of conformational changes of proteins, preferably in connection with infections by viruses or bacteria and/or by new proteins formed in association with neoplasias.

Also preferred is the use of inhibitors of Notch activation in the production of a medicament for inhibiting induction and/or expression of interleukin-22 for the treatment of diseases, preferably dermal diseases.

Particularly good results were achieved in inflammatory dermal diseases and psoriasis. It was completely surprising to find that inhibitors of Notch activation can be used to effectively and quickly alleviate the symptoms of psoriasis.

A person skilled in the art will know whether or not IL-22 is expressed in a particular disease. If the course of a disease, such as the course of inflammatory dermal diseases, is associated with the production of IL-22, the teaching of the invention can be used to inhibit IL-22 induction and/or expression.

In another preferred embodiment of the invention it is envisaged to inhibit the activation of Notch in T cells so as to achieve a reduction of the IL-22 production. This can be achieved by pharmacological inhibition of the Notch signal (a person skilled in the art will be familiar with methods of pharmacologically inhibiting Notch activation, e.g. by using the γ-secretase inhibitor class of active substances) or by administering antibodies against Notch ligands (especially the Delta-like family, and in particular against Delta-like 4) or by means of parts of ligands or peptides or other molecules preventing the signal-activating interaction between Notch and Notch ligands.

In another aspect the invention relates to the use of the inventive method for modulating inflammations.

The invention also relates to the use of Notch regulators in the production of a medicament to inhibit inflammations, especially for the treatment of diseases selected from the group comprising Hashimoto's thyroiditis, primary myxedema, thyrotoxicosis (Basedow's disease), pernicious anemia, Addison's disease, myasthenia gravis, juvenile diabetes mellitus, Goodpasture's syndrome, autoimmune hemolytic anemia, autoimmune leukopenia, pemphigus vulgaris, sympathetic ophthalmia, primary biliary cirrhosis, in particular primary biliary liver cirrhosis, autoimmune hepatitis, especially chronic aggressive autoimmune hepatitis, Sjogren's syndrome, rheumatoid arthritis, rheumatic fever, systemic lupus erythematosus, dermatomyositis/polymyositis, progressive systemic sclerosis, Wegener's granulomatosis, polyarteritis nodosa, hypersensitivity angiitis, thyrotoxicosis, thyroid-caused myxedema, generalized endocrinopathy, chronic gastritis type A, autoimmune diseases of single or all corpuscular elements of the blood, particularly idiopathic thrombocytopenia or thrombocytopathy, idiopathic leukopenia, agranulocytosis, pemphigoid, uveitis, diabetes mellitus type I, Crohn's disease, ulcerative colitis, Addison's disease, lupus erythematosus disseminatus and discoid form of said disease, as dermatomyositis and scleroderma, rheumatoid arthritis (=primary chronic polyarthritis), antiglomerular basement membrane nephritis, an aggressive immune reaction due to breakdown of the immune tolerance to self-determinants and reduction of the activity of T suppressor cells, preferably with lymphocyte marker T8 or excess of T helper cells, preferably with lymphocyte marker T4 via suppressor cells; formation of autoantigens, particularly by coupling of host proteins to haptens, preferably drugs, immune reactions caused by ontogenetic tissue not developing until self-tolerance has developed, by protein components demasked as a result of conformational changes of proteins, preferably in connection with infections by viruses or bacteria and/or by new proteins formed in association with neoplasias.

In another preferred embodiment the invention relates to the use of the inventive method for inducing interleukin-22 in vitro or in vivo, especially in a patient, for the treatment of the above-mentioned diseases.

The invention is remarkable for the following advantages:

Departure from conventional technologies

New field of problems

Existence of a long-unsatisfied, urgent need for the solution of the problem solved by the invention Hitherto vain efforts in the art Simplicity of a particular solution indicates inventive activity, especially as it replaces more complicated teachings Development in scientific technology has proceeded in a different direction Achievement that rationalizes development Erroneous ideas in the art on the solution of the problem at issue (prejudice)

Technical progress, e.g. improvement, performance enhancement, lower expense, savings of time, materials, work steps, cost or raw materials difficult to obtain, enhanced reliability, elimination of flaws, superior quality, maintenance freedom, greater efficiency, higher yield, expansion of the technical scope, provision of a further means, creation of a second approach, creation of a new field, first-time solution of a problem, reserve means, alternatives, scope for rationalization, automation and miniaturization, or enrichment of the range of available drugs Fortunate choice out of a variety of possibilities because one has been selected, the result of which has not been predictable, this therefore being a patentable fortunate choice Errors in the technical literature or highly contradictory representation of the subject matter of the invention Young field of technology Combination invention, i.e., several known elements have been combined to achieve a surprising effect Issue of licenses Praise in the art Economic success.

More specifically, the advantageous embodiments of the invention have at least one or more of the above-mentioned advantages.

EXAMPLES

Without intending to be limiting, the invention will be explained in more detail below with reference to the examples.

Example 1

Naive, i.e. antigen-inexperienced, T helper cells are activated in vitro in the presence of interleukin-12 (Th1) or without IL-12 and retrovirally transduced with active Notch. After 5 days the cells are restimulated and IL-22 mRNA expression is analyzed. In some cases, IL-10-producing cells were isolated following restimulation. Control cells barely produce any IL-22 under these conditions. In contrast, Notch-transduced T helper cells produce large quantities of IL-22 both under Th1 and Th0 conditions. Moreover, IL-22 is produced by both IL-10-positive and IL-10-negative Th cells (FIG. 1).

Example 2

Figure 2:
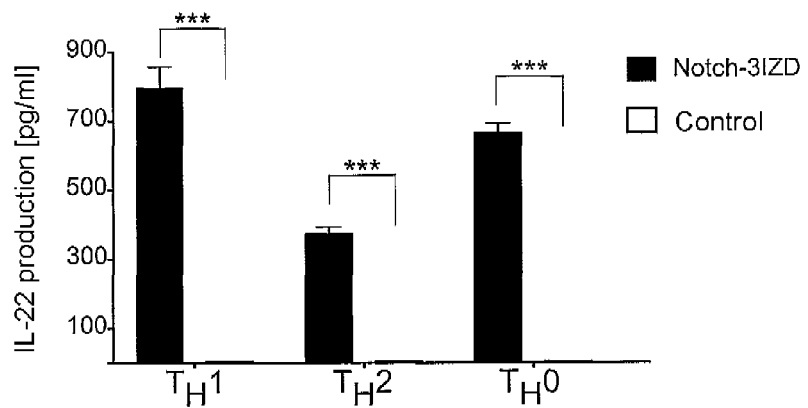
FIG. 2 shows that, in contrast to control-transduced T cells, Notch-transduced Th cells show strong IL-22 expression under all culture conditions, which is particularly pronounced in Th17 cells (FIG. 2A: Th1, Th2, Th0 cells.
Figure 2:
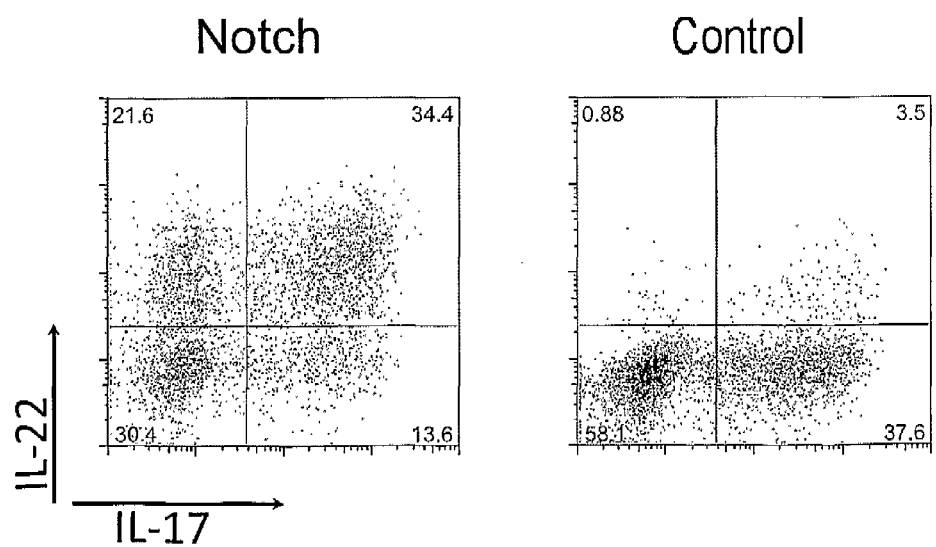

Naive, i.e. antigen-inexperienced, T helper cells are activated in vitro under Th1, Th2, Th0 conditions (FIG. 2A) or Th17 conditions (FIG. 2B) and retrovirally transduced with active Notch. After 5 days the cells are restimulated and IL-22 expression is analyzed. In contrast to control-transduced T cells, Notch-transduced Th cells show strong IL-22 expression under all culture conditions, which is particularly pronounced in Th17 cells (FIG. 2).

Example 3

Figure 3:
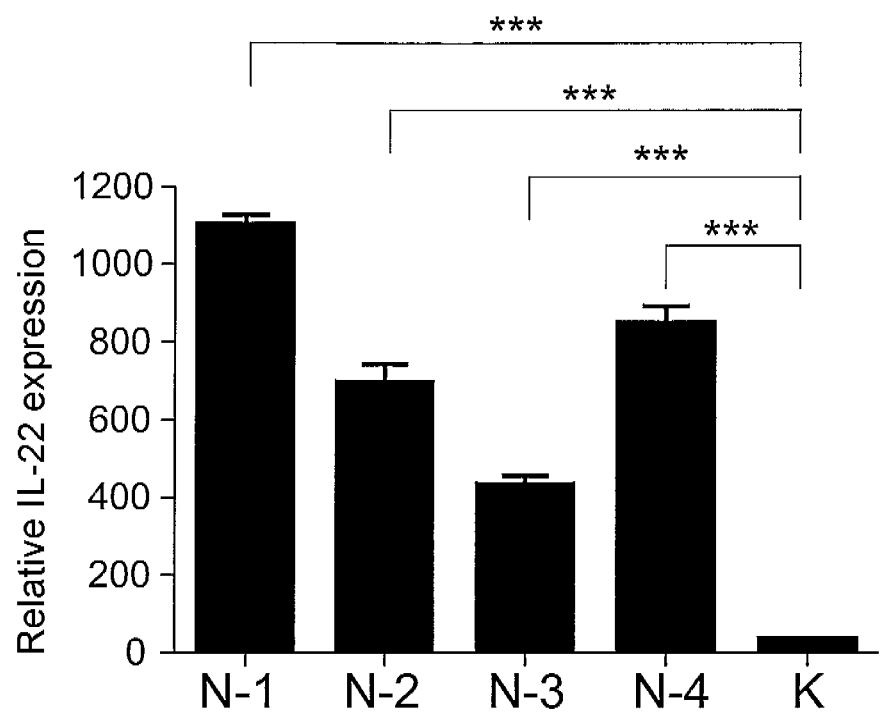
FIG. 3 shows that all four Notch isoforms can induce IL-22.

Naive, i.e. antigen-inexperienced, T helper cells are activated in vitro in the presence of interleukin-12 (Th1) and retrovirally transduced with active Notch (Notch 1 through Notch-4). After 5 days the cells are restimulated and IL-22 mRNA expression is analyzed. It can be seen that all four Notch isoforms can induce IL-22 (FIG. 3).

Figure 4:
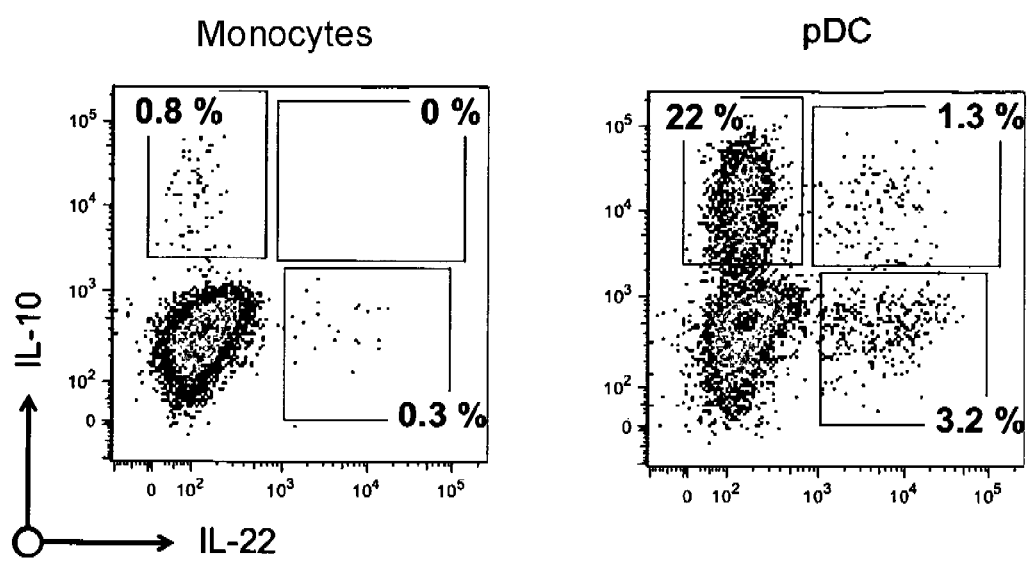
FIG. 4 shows that plasmacytoid dendritic cells can induce expression of both IL-22 and IL-10 in Th cells.

Naive, i.e. antigen-inexperienced, human T helper cells are co-cultured with monocytes or plasmacytoid dendritic cells and activated. The pDCs or monocytes are activated using the TLR-9 agonist CpG. After 5 days the cells are restimulated and the expression of IL-22 and IL-10 is analyzed. It can be seen that plasmacytoid dendritic cells can induce expression of both IL-22 and IL-10 in Th cells (FIG. 4).

Example 4

Figure 5:
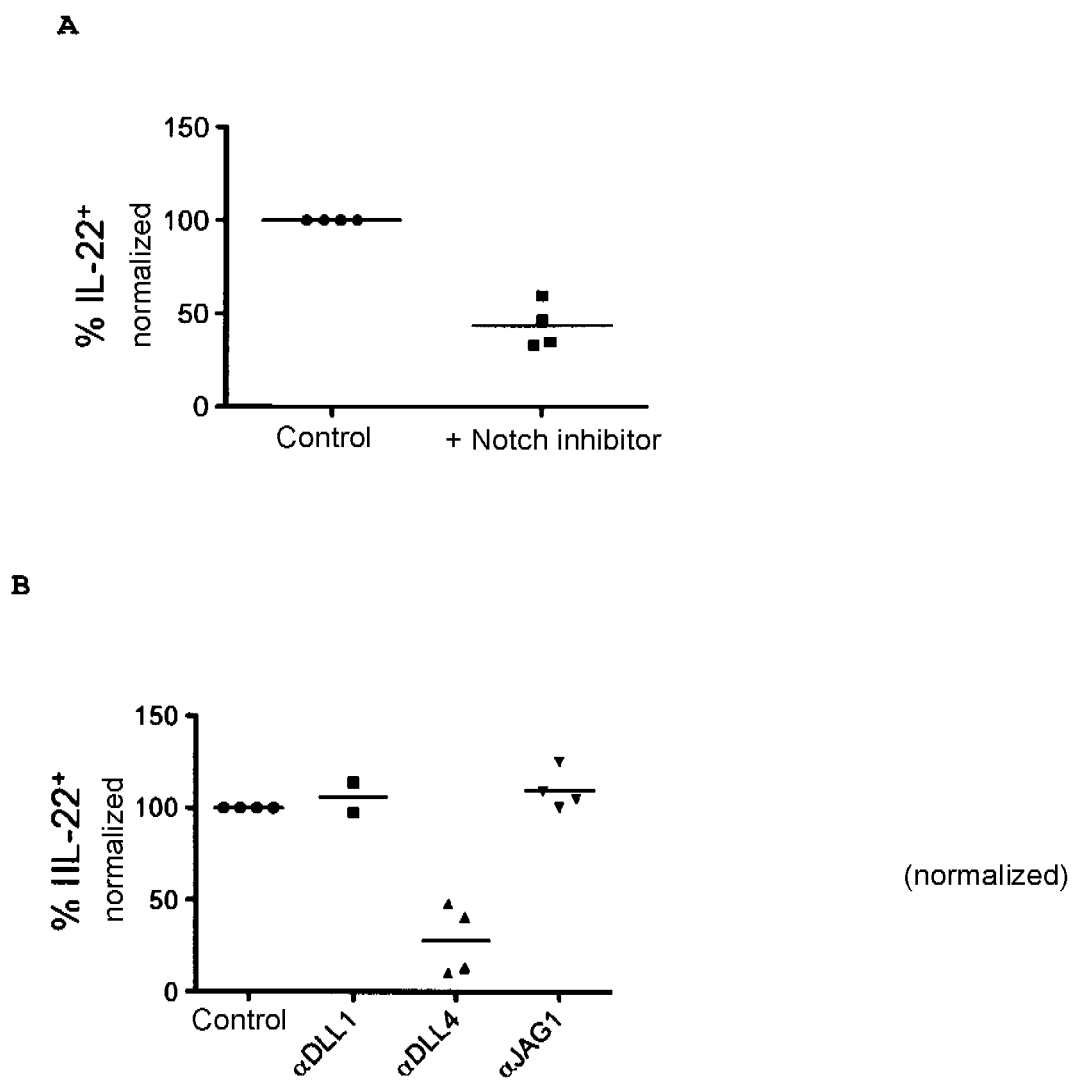

Naive, i.e. antigen-inexperienced, human T helper cells are co-cultured with plasmacytoid dendritic cells and activated. The pDCs are activated using the TLR-9 agonist CpG. In some batches the Notch signaling pathway is inhibited by a specific inhibitor (γ-secretase inhibitor) (FIG. 5A). In some batches the interaction of Notch with Jagged or with Dll-1 and Dll-4 is selectively inhibited by blocking antibodies (FIG. 5B). After 5 days the cells are restimulated and the expression of IL-22 is analyzed. It can be seen that plasmacytoid dendritic cells can induce expression of IL-22 in Th cells. This induction depends on the Notch activity (FIG. 4A). Furthermore, the above IL-22 expression is dependent on the ligands of the Delta-like family, especially Dll-4 (FIG. 5B).

Example 5

Figure 6:
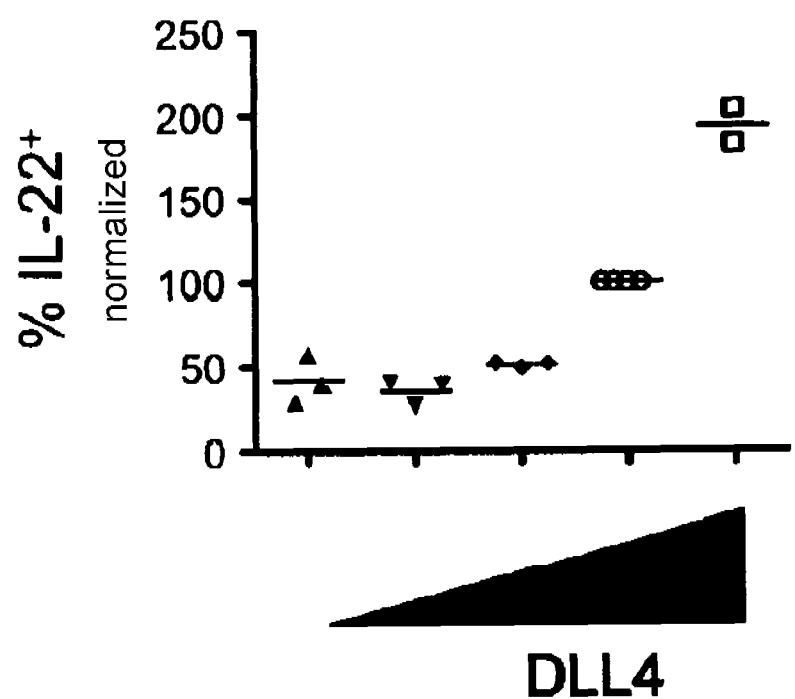
FIG. 6 shows that the Notch ligand Dll-4 results in concentration-dependent expression of IL-22.

Naive, i.e. antigen-inexperienced, human T helper cells are activated in the absence of antigen-presenting cells with microparticles loaded with stimulating anti-CD3 and anti- CD28 antibodies and increasing concentrations of recombinantly produced Delta-like 4. After 5 days the cells are restimulated and the expression of IL-22 is analyzed. It can be seen that the Notch ligand Dll-4 results in concentration-dependent expression of IL-22 (FIG. 6).

The invention claimed is:

1. A method for modulating interleukin-22 (IL-22) production in T helper cells comprising:
    contacting T helper cells with notch regulators selected from the group consisting of inducers of signal-active Notch molecules and/or Notch inhibitors, wherein the interleukin-22 production in said T helper cells is modulated and analyzing IL-22 production by said T helper cells.

2. The method of claim 1,
    wherein the T helper cells are selected from the group consisting of naive T cells, memory T cells, pro-inflammatory Th1 cells, pro-inflammatory Th2 cells and pro-inflammatory Th17 cells.

3. The method of claim 1,
    wherein the signal-active Notch molecules are induced by
    (i) physiological activation of Notch receptors, and/or
    (ii) transfection of T helper cells with constitutively active forms of Notch receptors.

4. The method of claim 3,
    wherein the Notch receptors are selected from the group consisting of Notch 1, 2, 3, 4 or combinations thereof.

5. The method of claim 3, wherein the Notch receptors are activated by Notch ligands, Notch ligand protein, Notch ligand fusion proteins, Notch ligand fragments, Notch ligand-expressing cells and/or stimulatory anti-Notch antibodies.

6. The method of claim 5, wherein the Notch ligands are Jagged family members and/or the Delta-like family members.

7. The method of claim 6, wherein the Jagged family members are Jagged 1 and/or 2 and/or the Delta-like family members are Delta-like 1, 2 and/or 4.

8. The method of claim 1,
    wherein the Notch molecules are endogenous Notch molecules.

9. The method of claim 1,
    wherein signal-active Notch 1, 2, 3 and/or 4 are overexpressed.

10. The method of claim 1,
    wherein Notch ligands are contacted with T helper cells, and said contacting is enhanced and/or induced by stimulation with antigen-presenting cells, and/or plasmacytoid dendritic cells.

11. The method of claim 10,
    wherein said contacting is enhanced and/or induced by stimulation of (i) antigen-presenting cells with Toll-like receptors or CD40 and/or (ii) plasmacytoid dendritic cells via Toll-like receptors or CD40.

12. The method of claim 1,
    wherein interleukin-22-producing T helper cells are generated in vitro by stimulation with Notch ligand protein, Notch ligand fusion proteins, signal-active Notch ligand fragments, Notch ligand-expressing cells and/or by introducing signal-active Notch using viral and/or non-viral transduction methods.

13. The method of claim 1,
    wherein IL-22-producing T helper cells are generated in vivo by contact with recombinant Notch ligands and/or by using Notch ligand-expressing cells.

14. The method of claim 1, wherein the inhibitors of Notch activation are selected from the group consisting of recombinant proteins, protein fragments and/or peptides of Notch or Notch ligands, pharmacological inhibitors, antibodies against Notch molecules or combinations thereof.

15. The method of claim 14,
    wherein expression of Notch ligands of the Delta-like family is inhibited in antigen-presenting cells and/or dendritic cells.

16. The method of claim 15, wherein said ligands are Delta-like 1 and Delta-like 4 ligands.

17. The method of claim 14, wherein the pharmacological inhibitors are γ-secretase inhibitors.

18. A method for generating interleukin-22 (IL-22)-producing T helper cells comprising:
    contacting T helper cells with signal-active Notch molecule inducers and/or signal-active Notch molecules, wherein the T helper cells become interleukin-22-producing T helper cells, and
    analyzing IL-22 production by said T helper cells.

19. A method of generating interleukin-22-producing T helper cells, comprising:
    contacting T helper cells with signal-active Notch molecules, wherein the Notch signaling pathway is activated, and
    analyzing interleukin-22-production by said T helper cells.

* * * * *